United States Patent [19]

DeVor

[11] Plant 4,613

[45] Jan. 6, 1981

[54] ROSE PLANT NAMED PAUL'S PINK

[75] Inventor: Paul F. DeVor, late of Pleasanton, Calif., by Thelma G. DeVor, executrix

[73] Assignee: DeVor Nurseries, Inc., Pleasanton, Calif.

[21] Appl. No.: 53,933

[22] Filed: Jul. 2, 1979

[51] Int. Cl.[3] ..... A01H 5/00

[52] U.S. Cl. ..... Plt./18

[58] Field of Search ..... Plt./18, 14, 26

*Primary Examiner*—Robert E. Bagwill

*Assistant Examiner*—James R. Feyrer

*Attorney, Agent, or Firm*—Chas. W. Rummler

[57] ABSTRACT

A new variety of hybrid tea rose plant having a profuse and continuous production of medium sized flowers of a very soft pink coloration and a strong, slightly spicy fragrance, the blooms opening beautifully with a high centered bud which is long lasting as an open flower and which has a very long lasting vase life. The plant itself is very vigorous and free branching in its growth habit, reaching a height of about four feet, with strong upright canes and stems and a moderate production of foliage.

3 Drawing Figures

BACKGROUND OF THE NEW PLANT

This new rose plant originated as a seedling resulting from a cross of Snowsong Supreme, U.S. Plant Pat. No. 2,624, and Pink Puff, U.S. Plant Pat. No. 2,634, made by the inventor at Livermore, Calif., in the course of breeding efforts to produce a hothouse variety combining the texture, keeping quality, fragrance and good imbrication of Snowsong Supreme with an unrelated fragrant, very productive floribunda variety Pink Puff to obtain a soft pink hybrid tea with increased production. In addition, it was desired to combine the leathery, vigorous and upright foliage of Pink Puff with the before mentioned good qualities of Snowsong Supreme.

This new plant was discovered by the inventor in 1971 and was subsequently asexually reproduced by him at Livermore, Calif., where further propagation by budding was carried on to test its capability of retaining its distinctive characteristics. Propagation of this plant by budding, through successive generations at Livermore, Calif., as well as Pleasanton and Hamilton City, Calif., has shown that the distinctive characteristics of the new variety hold true from generation to generation and appear to be firmly fixed.

DESCRIPTION OF THE DRAWINGS

This new variety of rose plant is illustrated by the accompanying photographic drawings which, in full color, show in FIG. 1 a full face view of a newly opened flower.

DESCRIPTION OF THE NEW PLANT

Figure 1:
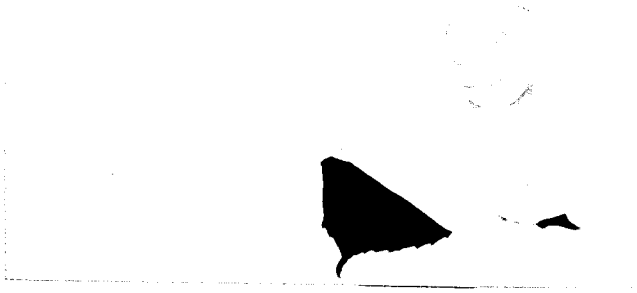
Figure 2:
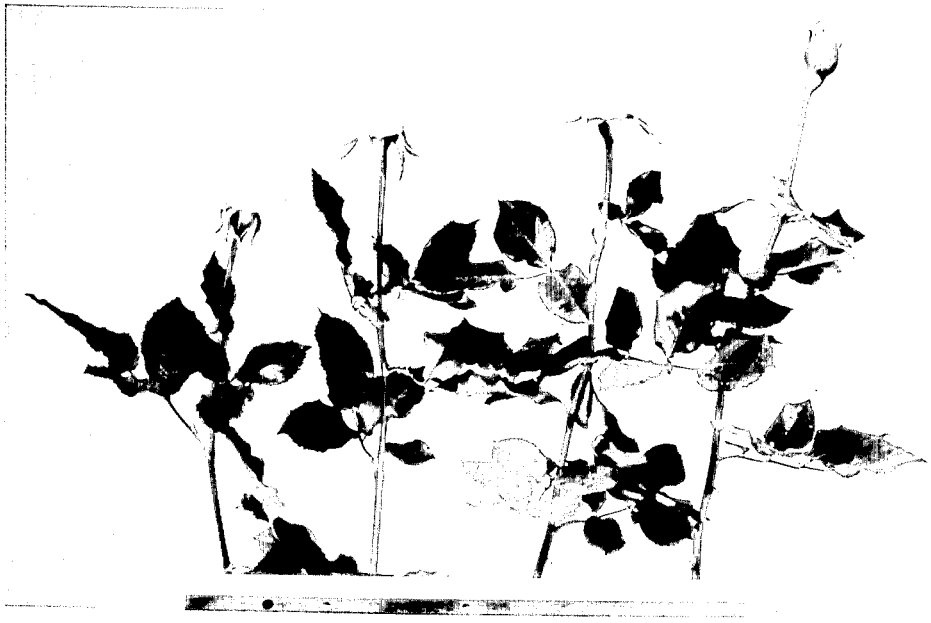
in FIG. 2 four stages of the bloom from a tight bud with sepals just cracked to a fully opened flower; and in FIG. 3 parts of the plant including top and bottom sides of typical foliage, a newly cracked bud and the form of the sepals, young wood, and two pieces of mature wood. The colors shown are as nearly true as can be reasonably expected to be reproduced by conventional photographic procedures.
Figure 3:
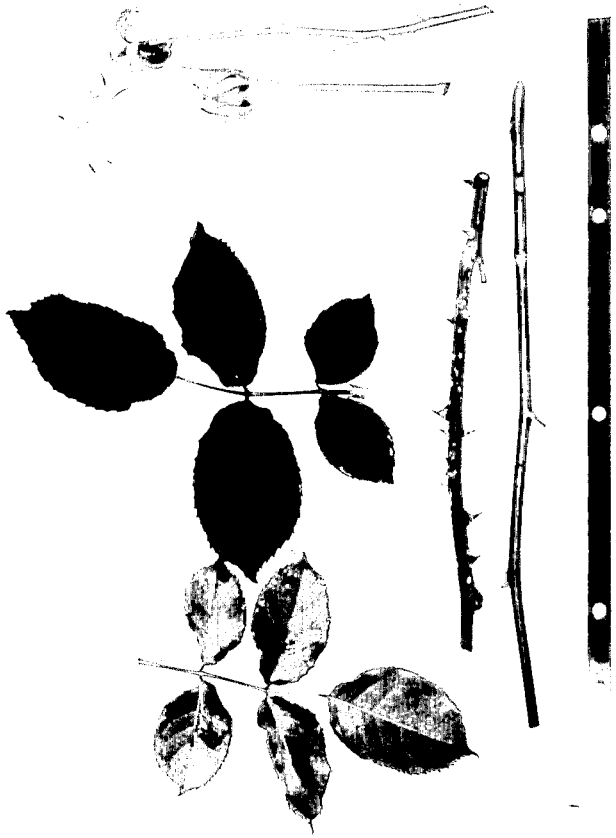

The following is a description, in detail, of this new variety of rose plant with color designations according to The RHS Colour Chart published by The Royal Horticultural Society of London, England, in collaboration with The British Colour Council, the following date being from observations of greenhouse plants made at Pleasanton, Calif.

THE PLANT

Origin: Seedling.

Parentage:

*Seed parent.*—Snowsong Supreme, U.S. Plant Pat. No. 2,624.

*Pollen parent.*—Pink Puff, U.S. Plant Pat. No. 2,634.

Classification:

*Botanic.*—Hybrid Tea.

*Commercial.*—Greenhouse Rose.

Form: Upright bush.

Height: About 4 feet.

Growth: Sturdy and very vigorous.

Habit: Free branching with strong canes and stems.

Foliage:

*Quantity.*—Moderate.

*Leaves.*—Number: 6 to 7 leaves on cut flower stem of normal length. Size: About 4 to 4½ inches wide and about 5 to 5½ inches long. Shape: Odd pinnate. Leaflets: 3 to 5 in number. Size: About 1⅛ to 1¼ inches wide by 1¾ to 2 inches long. Shape: Ovate, with serrate margin and cuspidate apex. Color: Upper side — Green 137B. Under side — Yellow Green 148C. Texture: Smooth and undulating. Aspect: Dull.

Petiolule: ⅛ inch long by 1/16 inch wide.

Petioles: ¾ to 1½ inches long from stem and ⅜ to ⅞ inch long from top of auricle.

Rachis: 1½ to 3¾ inches long, stipules adnate with very low minute hairs.

Thorns: Very few in number.

*Size.*—⅜ inch long and curving downward from a ⅜ inch wide base.

*Color.*—Yellow Green 145C.

THE BUD

Before bud breaks:

*Size.*—1¾ inches long and 1¼ to 1½ inches in diameter.

*Form.*—Long urn-shaped.

*Opening.*—The bud opens slowly.

When sepals first divide:

*Size.*—Length — 2 to $2\frac{1}{4}$ inches. Diameter: Across center — $1\frac{1}{2}$ to $1\frac{3}{4}$ inches. Across base — $1\frac{1}{8}$ to $1\frac{1}{4}$ inches.

*Color.*—Red 51C.

When petals begin to unfurl:

*Color.*—Red 49D.

Sepals: The sepals are branched and spear-shaped, every other sepal has 2 small bracts and 2 large bracts, and the sepals curl back as the bud elongates and the flower opens.

*Color.*—Inside — Yellow Green 147D. Outside — Green 143C.

Calyx:

*Shape.*—Pear-shaped.

*Size.*—Medium, $\frac{1}{2}$ inch wide and $\frac{5}{8}$ inch long.

*Aspect.*—Smooth.

*Splitting.*—Calyx does not split.

Peduncle:

*Length.*—About $2\frac{5}{8}$ to $3\frac{1}{4}$ inches long.

*Aspect.*—Very smooth and shiny with no small hairs or evident glands.

*Strength.*—Erect and slender.

*Color.*—On side facing sunlight — Yellow Green 144B. On shaded side — Yellow Green 144C.

THE FLOWER

Blooming habit: Profusely and continuously the year around under glass, blooming freely in fall and winter.

Size: Medium; $3\frac{1}{2}$ inches in diameter and $1\frac{3}{4}$ inches in depth.

Borne: Singly.

Shape:

*When bloom first opens.*—High centered.

*As bloom matures.*—The petals fall back but petaloids cover the center.

Petalage:

*Number of petals.*—26 to 30.

*Arrangement.*—Imbricated.

*Form.*—Ruffled margin with petals curling slightly outward.

*Texture.*—Firm.

*Aspect.*—Satiny.

*Color.*—Outer petals: Top side — Red 36D with Yellow Green 150C at base. Reverse side — A range of Red 49D to 55D at margin, Red 49C at center and Yellow Green 150B at base. Inside petals: Top side — Margin, Red 49D with Yellow Green 150D at base. Reverse side — Red 49B at margin, Red 50D at center and Yellow Green 149D at base.

*Petaloids.*—Number: 2 to 4. Size: $\frac{1}{4}$ inch wide and $\frac{1}{2}$ inch long. Color: Red 38D with Yellow Green 154C at base.

Peduncle:

*Length.*—$2\frac{5}{8}$ to $3\frac{1}{4}$ inches long.

*Color.*—Yellow Green 144C.

*Character.*—Upright, slender, erect, strong and wiry.

Persistence: The petals drop cleanly after full bloom.

Fragrance: Strong and very slightly spicy.

Lasting quality: Long lasting on the plant and very long lasting as a cut flower.

REPRODUCTIVE ORGANS

Stamens:

*Anthers.*—97 to 104 in number. Arrangement: Slightly introrse. Length: 5/16 inch. Color: Yellow Orange 19C.

*Filaments.*—Length: 5/16 to 7/16 inch. Color: Yellow Green 154D at base and Yellow White 158D near anthers.

*Pollen.*—Color: Yellow Orange 19A.

Pistils:

*Number.*—45 to 50.

*Styles.*—$\frac{1}{2}$ inch long.

*Stigmas.*—Yellow White 158A.

Ovaries: Very slender and covered with silvery white hair. Styles are unattached throughout.

FRUIT

The fruit is fertile and pear-shaped in form. Its color at maturity is Orange 26B.

The distinctive qualities of this new variety of rose plant reside in its consistent and profuse production of fine quality blooms throughout the entire year as a greenhouse plant, its beautifully opening high centered bud which is very long lasting as an open flower having a unique and very soft pink coloration and a strong fragrance. This plant is further characterized by its very vigorous and free branching growth habit producing strong canes and stems and a moderate quantity of foliage.

It is claimed:

1. A new and distinct variety of rose plant substantially as herein shown and described, characterized by its beautifully opening high centered blooms which have a very soft pink coloration and strong fragrance, its vigorous and free branching growth habit, and its profuse year-around production of long lasting flowers.

* * * * *